United States Patent
Rigby

Patent Number: 5,910,115
Date of Patent: Jun. 8, 1999

[54] METHOD AND APPARATUS FOR COHERENCE FILTERING OF ULTRASOUND IMAGES

[75] Inventor: Kenneth Wayne Rigby, Clifton Park, N.Y.

[73] Assignee: General Electric Company, Schenectady, N.Y.

[21] Appl. No.: 08/934,692

[22] Filed: Sep. 22, 1997

[51] Int. Cl.⁶ .................................................. A61B 8/00
[52] U.S. Cl. ............................................................ 600/443
[58] Field of Search .................................. 600/443, 447; 73/625–626

[56] References Cited

U.S. PATENT DOCUMENTS 5,476,098  12/1995  O'Donnell .............................. 600/447

OTHER PUBLICATIONS

Reiter et al., "A Semblance–Guided Median Filter", Geophys. Prospect., vol. 51, pp. 15–41 (1993).

Szabo et al., "Velocity Guided Median Filtering Applications To Ultrasonic Imaging", 23rd International Symposium of Acoustical Imaging, Boston, MA, Apr. 13–16, 1997. Printed by Brattleboro Printing, Inc., 11 Elm St., Brattleboro, VT 05303–248.p.

*Primary Examiner*—Francis J. Jaworski
*Attorney, Agent, or Firm*—Noreen C. Johnson; Douglas E. Stoner

[57] ABSTRACT

A method and apparatus for improving medical ultrasound images employs data-dependent filtering. A quantity, called the coherence factor, is calculated for each pixel in the image. The coherence factor is defined to be the ratio of two quantities: the amplitude of the receive signals summed coherently and the amplitude of the receive signals summed incoherently. The coherence data is stored in buffer memory and is optionally spatially filtered and mapped. The amplitude data is concurrently acquired and stored in buffer memory. The system can be selectively operated to display the coherence information alone, the amplitude information alone, or a combination of the coherence and amplitude information.

16 Claims, 4 Drawing Sheets

METHOD AND APPARATUS FOR COHERENCE FILTERING OF ULTRASOUND IMAGES

FIELD OF THE INVENTION

This invention generally relates to digital ultrasound imaging systems and, in particular, to methods for improving medical ultrasound images by means of data-dependent filtering.

BACKGROUND OF THE INVENTION

A conventional ultrasound imaging system comprises an array of ultrasonic transducer elements which are used to transmit an ultrasound beam and then receive the reflected beam from the object being studied. Such scanning comprises a series of measurements in which the steered ultrasonic wave is transmitted, the system switches to receive mode after a short time interval, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delays (and/or phase shifts) and gains to the signal from each receiving transducer element. The output signals of the beamformer channels are then coherently summed to form a respective pixel intensity value for each point of focus, corresponding to a sample volume in the object region or volume of interest. These pixel intensity values are log-compressed, scan-converted and then displayed as an image of the anatomy being scanned.

Tissue types and anatomical features are most easily differentiated in an ultrasound image when they differ in image brightness. Image brightness on conventional medical ultrasound imaging systems is a function of the receive beamformed signal amplitude, i.e., after coherent summation of the delayed receive signals on each transducer element. More precisely, the logarithm of the beamformed signal amplitude is displayed, with user-adjustable gain and contrast, and, if desired, a choice of a handful of grayscale mapping tables.

A human kidney usually appears in an ultrasound image as a darkish, ellipsoidal region (corresponding to the renal cortex) with a bright, irregularly shaped interior (the medulla). One criterion used by sonographers to evaluate ultrasound image quality is the contrast (i.e., the displayed difference in brightness) between the renal cortex and the medulla. This can be artificially increased by adjusting the grayscale maps manually after the fact, but this approach is of little practical value. Much more desirable would be the identification of another tissue contrast mechanism which could be used in addition to the receive amplitude to distinguish tissue types.

SUMMARY OF THE INVENTION

The present invention is a method and apparatus for improving medical ultrasound images by utilizing data-dependent filtering. The filter increases contrast between tissue types by distinguishing them on the basis of the degree of coherence of the receive ultrasound signals. The method also provides some suppression of speckle noise without significantly degrading resolution. The method can be implemented in real-time with only a modest change to the hardware of an existing ultrasound imaging system. The invention can be incorporated in the beamforming system of a digital ultrasound imaging system having either a baseband beamformer or a pure time-delay beamformer (also known as an RF beamformer).

In accordance with the method of the invention, a quantity, called the coherence factor, is calculated for each pixel in the image. The coherence factor is defined to be the ratio of two quantities: the amplitude of the receive signals summed coherently and the amplitude of the receive signals summed incoherently. The coherence data is stored in buffer memory and is optionally spatially filtered and mapped. The amplitude data is concurrently acquired and stored in buffer memory.

The system of the invention can be selectively operated to display the coherence information alone, the amplitude information alone, or a combination of the coherence and amplitude information. In accordance with the preferred embodiment, this combination consists of multiplying, sample by sample, the receive beamformed amplitude by the coherence factor, and then displaying the modified amplitude conventionally, i.e., by log-compressing and scan-converting.

DETAILED DESCRIPTION OF THE PREFERRED EMBODIMENTS

Figure 1:
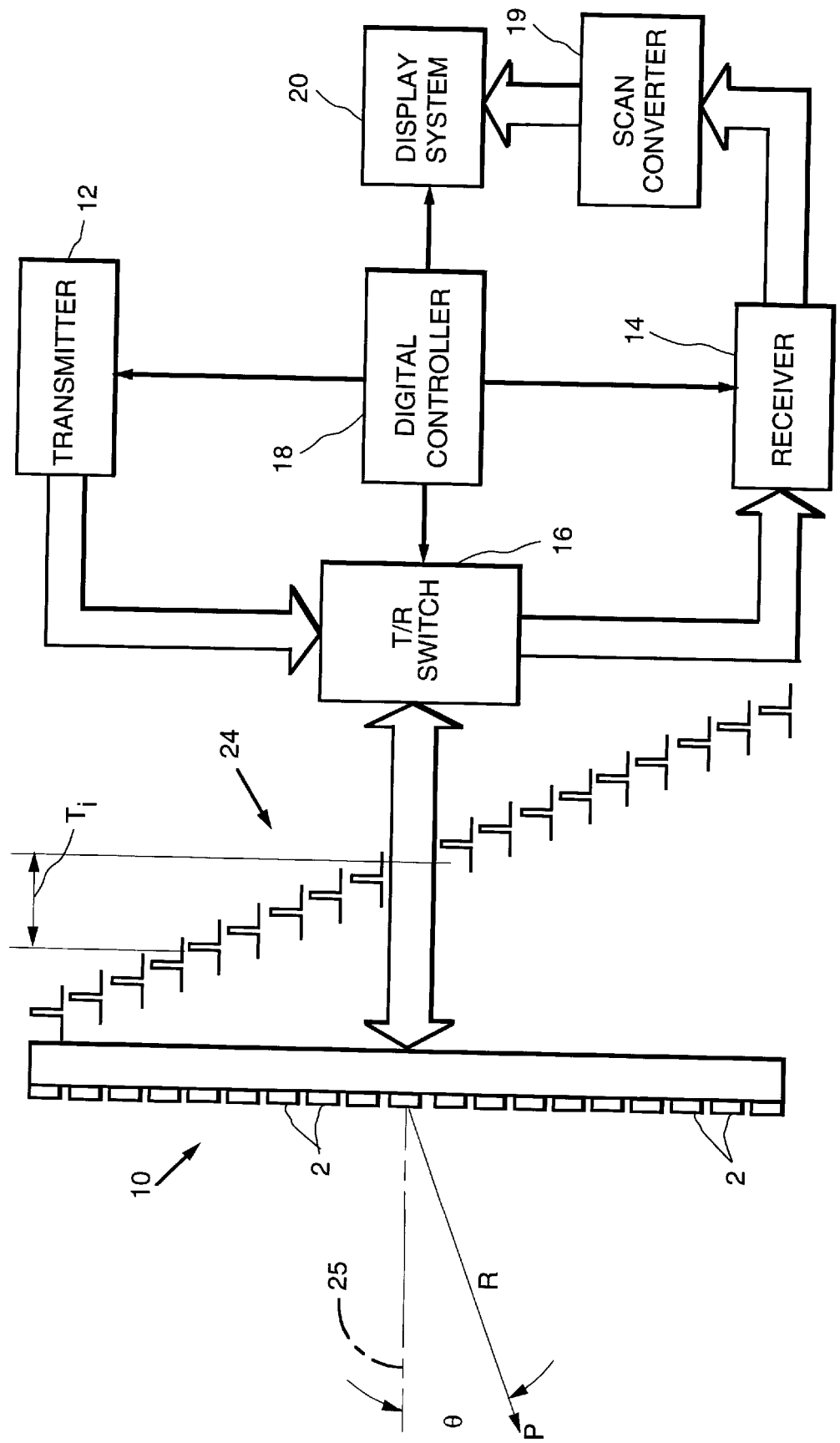
FIG. 1 is a block diagram of an ultrasonic imaging system which incorporates the present invention.

As shown in FIG. 1, the ultrasonic imaging system incorporating the invention includes a transducer array 10 comprised of a plurality of separately driven transducers 2, each of which produces a burst of ultrasonic energy when energized by a pulsed waveform produced by a transmitter 12. The ultrasonic energy reflected back to transducer array 10 from the object under study is converted to an electrical signal by each receiving transducer 2 and applied separately to a receiver 14 through a set of transmit/receive (T/R) switches 16. Transmitter 12, receiver 14 and switches 16 are operated under control of a digital controller 18 responsive to commands by a human operator. A complete scan is performed by acquiring a series of echoes in which switches 16 are set to their transmit positions, transmitter 12 is gated ON momentarily to energize each transducer 2, switches 16 are then set to their receive positions, and the subsequent echo signals produced by each transducer 2 are applied to receiver 14. The separate echo signals from each transducer 2 are combined in receiver 14 into a single echo signal which is used to produce a line in an image on a display system 20.

Transmitter 12 drives transducer array 10 such that the ultrasonic energy produced is directed, or steered, in a beam. To accomplish this, transmitter 12 imparts a time delay $T_i$ to the respective pulsed waveforms 24 that are applied to successive transducers 2. By adjusting the time delays $T_i$ appropriately in a conventional manner, the ultrasonic beam can be directed away from axis 25 by an angle θ and focused at a fixed range R. A sector scan is performed by progressively changing the time delays $T_i$ in successive excitations. The angle θ is thus changed in increments to steer the transmitted beam in a succession of directions.

The echo signals produced by each burst of ultrasonic energy reflect from objects located at successive ranges along the ultrasonic beam. The echo signals are sensed separately by each transducer 2 and a sample of the echo signal magnitude at a particular point in time represents the amount of reflection occurring at a specific range. Due to the differences in the propagation paths between a reflecting point P and each transducer 2, however, these echo signals are not detected simultaneously. Receiver 14 amplifies the separate echo signals, imparts the proper time delay to each, and sums them to provide a single echo signal which accurately indicates the total ultrasonic energy reflected from point P located at range R along the ultrasonic beam oriented at the angle θ.

To simultaneously sum the electrical signals produced by the echoes impinging on each transducer 2, time delays are introduced into each separate channel 34 (see FIG. 2) of receiver 14. The beam time delays for reception are the same delays $T_i$ as the transmission delays described above. However, the time delay of each receive channel continuously changes during reception of the echo to provide dynamic focusing of the received beam at the range R from which the echo signal emanates.

Under direction of digital controller 18, receiver 14 provides delays during the scan such that steering of receiver 14 tracks the direction θ of the beam steered by transmitter 12 and samples the echo signals at a succession of ranges R so as to provide the proper delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

A scan converter 19 receives the series of data points produced by receiver 14 and converts the data into the desired image. More particularly, the scan converter converts the acoustic image data from polar coordinate (R–θ) sector format or Cartesian coordinate linear array to appropriately scaled Cartesian coordinate display pixel data at the video rate. This scan-converted acoustic data is then supplied to a display monitor (not shown) of a display system 20, which images the time-varying amplitude of the signal envelope as a grey scale.

Figure 2:
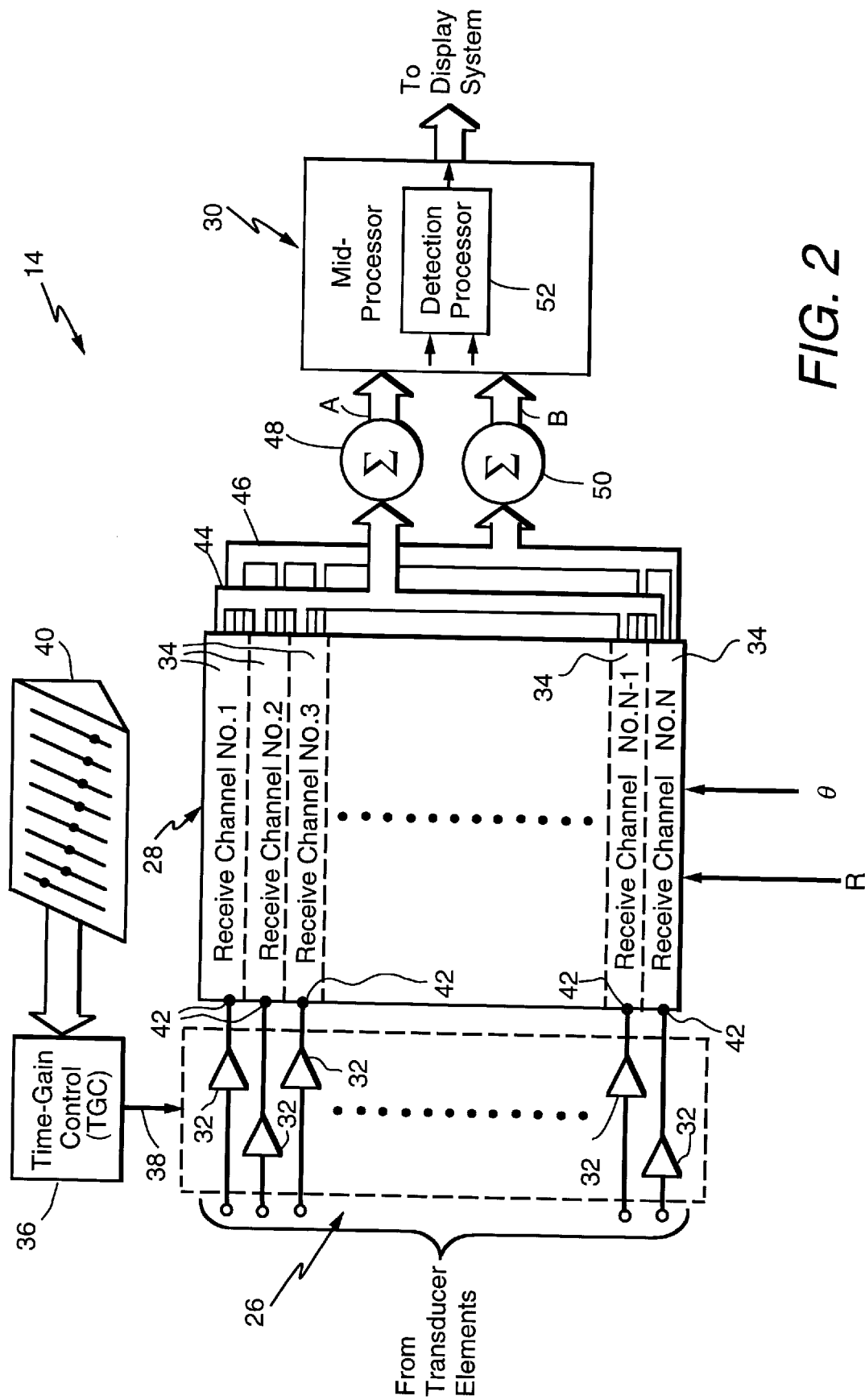
FIG. 2 is a block diagram showing of a receiver which forms part of the system of FIG. 1.

As shown in FIG. 2, receiver 14 comprises three sections: a time-gain control section 26, a receive beamforming section 28 and a mid-processor 30. Time-gain control (TGC) section 26 includes a respective amplifier 32 for each of the receive channels 34, and a time-gain control circuit 36 is provided for controlling gain of amplifiers 32. The input of each amplifier 32 is coupled to a respective one of transducers 2 to amplify the echo signal which it receives. The amount of amplification provided by amplifiers 32 is controlled through a control line 38 driven by TGC circuit 36, the latter being set by hand operation of potentiometers 40.

The receive beamforming section of receiver 14 includes a multiplicity of receive channels 34, each receive channel 34 receiving the analog echo signal from a respective amplifier 32 at a respective input 42. The analog signals are digitized and produced as a stream of signed digitized samples. These samples are respectively delayed in the receive channels such that when they are summed with samples from each of the other receive channels, the amplitude of the summed signals is a measure of the strength of the echo signal reflected from a point P located at range R on the steered beam θ.

Figure 3:
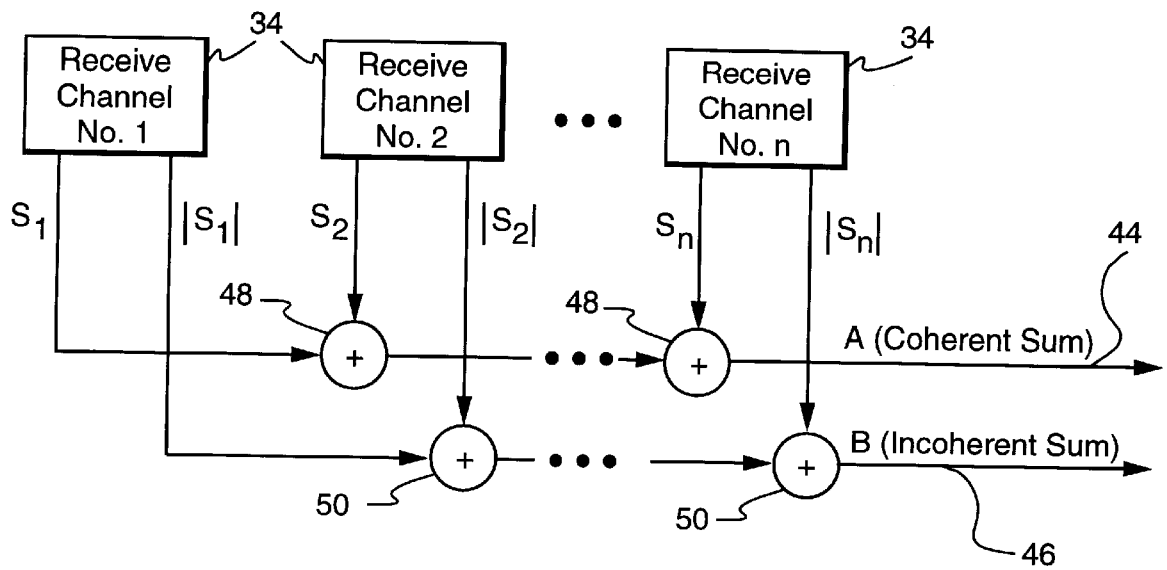
FIG. 3 is a block diagram showing the receiver of FIG. 2 in more detail.

As shown in FIG. 3, each receive channel 34 supplies, in addition to the delayed signed samples, the amplitude, or absolute value, of the delayed signed samples. As shown in FIG. 3, the delayed signed samples are provided to a coherent summation bus 44, while the amplitudes of the delayed, signed samples are provided to an incoherent summation bus 46. Coherent summation bus 44 sums the delayed signed samples from each receive channel 34 using pipeline summers 48 to produce coherent sum A. Incoherent summation bus 46 sums the amplitudes of the delayed signed samples from each receive channel 34 using pipeline summers 50 to produce incoherent sum B.

Receiver midprocessor section 30, as shown in FIG. 2, receives the coherently summed beam samples from summers 48 via output A and receives the incoherently summed beam samples from summers 50 via output B. Midprocessor section 30 comprises a detection processor 52, which is shown in more detail in FIG. 4.

Detection processor 52 calculates and applies a coherence factor C in accordance with the present invention. The coherence factor is calculated for each pixel in the image and is defined to be the ratio of two quantities: the amplitude of the sum of the receive signals and the sum of the amplitudes of the receive signals, or $$C = \left| \sum_{i=1}^{N} S_i \right| \bigg/ \sum_{i=1}^{N} |S_i| \qquad (1)$$

where $s_i$ is the delayed signal for the i-th transducer element. This ratio is calculated in detection processor 52, shown in FIG. 4, by calculating the absolute value of the coherent sum A in a summer 54 and then calculating the ratio of the absolute value of the coherent sum A to the incoherent sum B in a divider 56, i.e., C=|A|/B.

For the case of a pure time-delay beamformer, the signal from each channel is a real, signed quantity and the coherent sum is the arithmetic sum of these signals. The incoherent sum is the arithmetic sum of the absolute value of each signal, i.e., a sum of non-negative numbers.

For the case of a baseband beamformer, the channel signals are complex numbers I+iQ, with real part I and imaginary part Q. The coherent sum is the sum of these complex numbers and is also complex. The absolute value of this coherent sum is a real, non-negative number, i.e., $(I^2+Q^2)^{1/2}$. This is the usual signal which is log-compressed, scan-converted and displayed. The incoherent sum for the baseband beamformer is the sum of the absolute values of each (complex) channel signal, i.e., a real, non-negative number.

Thus the coherence factor C is a real, non-negative quantity. The minimum value of C is zero, since it is the ratio of two non-negative numbers. The denominator in Eq. (1) can vanish only if all the $s_i$'s are zero. In this case, the numerator also vanishes, so C is defined as zero in this case. The maximum value of C is unity. This follows from Bessel's inequality:

$$|A+B| \leq |A|+|B| \qquad (2)$$

where A and B are any two vectors. C equals unity only when $s_i$ is a constant independent of i, which is when the receive signals are perfectly coherent, i.e., identical, across the transducer array.

Spatially filtering the coherence factor can be advantageous because—like the normal amplitude image—the coherence factor suffers from speckle noise. The coherence information can be spatially filtered to reduce this speckle noise without significantly degrading the apparent resolution of the final image in those cases (transparent overlay and modified grayscale, described below) in which the coherence data is not displayed independently. For example, the coherence factor can be filtered with a simple 5×5 filter which substitutes the average of the 25 values for the center value in the 5×5 filter kernel. The use of spatial filtering increases the contrast between the bright and dark areas of the kidney, for example, and within fat and muscle layers.

Figure 5:
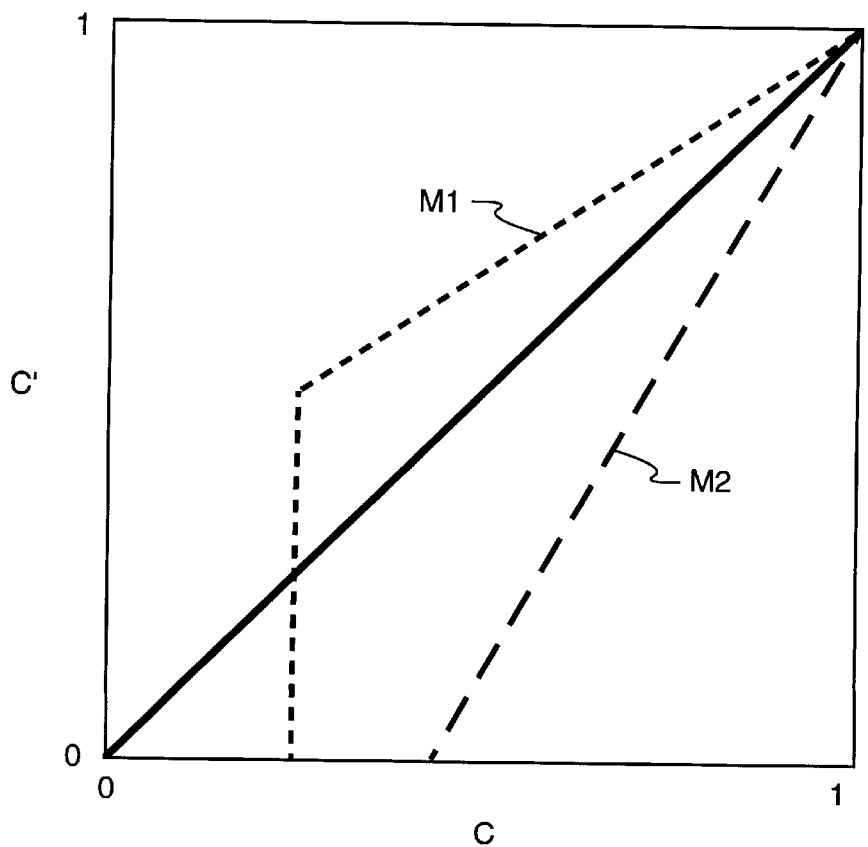
FIG. 5 is a graph showing mappings for the coherence factor C in accordance with first and second preferred embodiments of the invention. The solid line is the default (no mapping) and the dashed lines show two linear mappings with thresholds.

In accordance with a further optional aspect of the invention, the coherence factor can be mapped before it is displayed or applied to the amplitude image, in order to optimize the coherence data for particular imaging applications. For example, the alternate mapping M1 shown in FIG. 5 will zero out the data (C=0) when the coherence factor C falls below a predetermined threshold. Similarly alternate mapping M2 zeros out the data at another threshold. This can be useful in cases where the primary diagnostic concern is identifying blood vessels in an image.

The coherence factor C provides independent information about the tissue and can be displayed as a separate image or as a transparent color map overlaid on the B-mode image. Alternatively, the coherence information can be combined with the amplitude information and displayed as a single grayscale image. In the simplest case, this combination consists of multiplying, sample by sample, the receive beamformed amplitude by the coherence factor, and then displaying the modified amplitude conventionally (by log-compressing and scan-converting).

Figure 4:
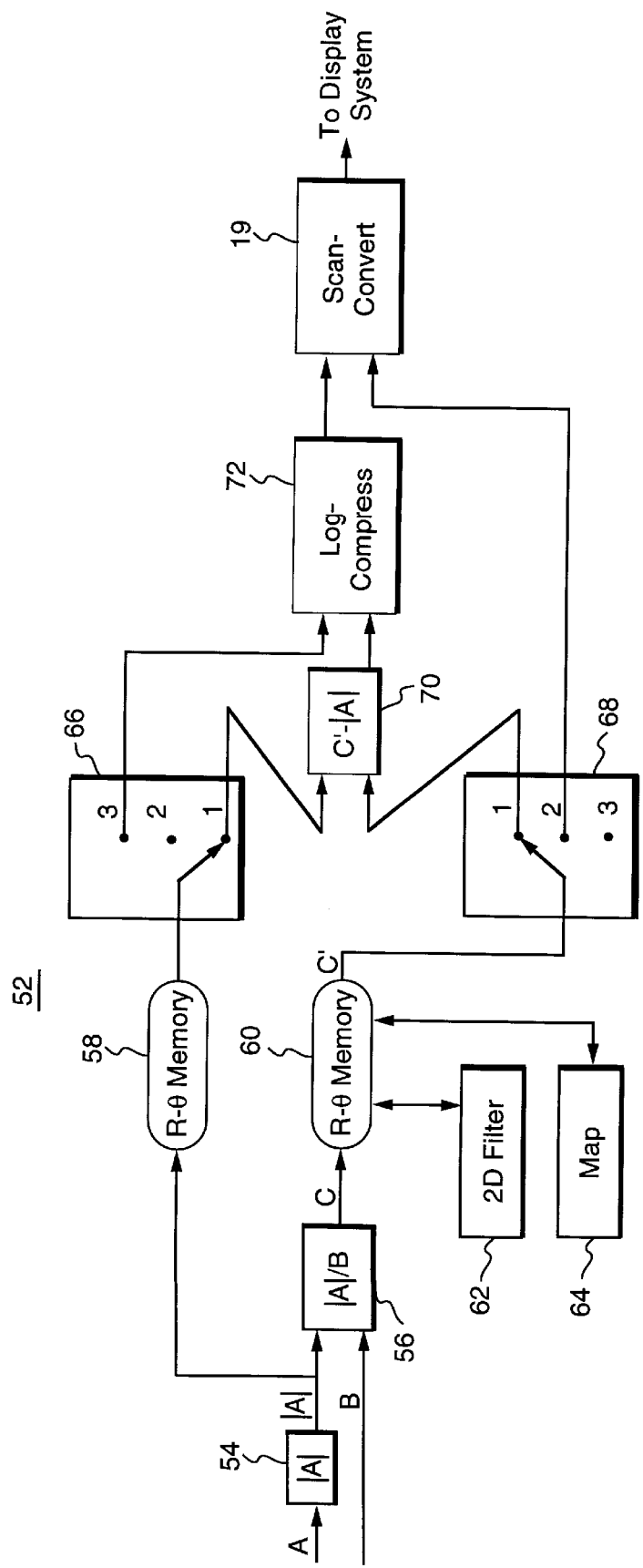
FIG. 4 is a block diagram showing the detection processor of FIG. 2 in more detail.

FIG. 4 depicts a system which can be selectively operated to display the coherence information alone, the amplitude information alone, or a combination of the coherence and amplitude information. In accordance with the preferred embodiment of the invention, the amplitude of the coherent sum, i.e., |A|, is placed into an R–θ memory buffer 58 which holds the samples for each range R and for each scan line direction θ. The coherence factor C, calculated as described above, is placed into a separate R–θ memory buffer 60. As mentioned above, the coherence information may optionally be filtered and scaled. The filtering and scaling operations are performed in buffer 60 by applying a two-dimensional filter 62 and a coherence map 64. The filtered and scaled coherence factor data is indicated by output C' in FIG. 4.

The output signal |A| of memory 58 is supplied to the input of a three-position switch 66. When switch 66 is set to position 1, the input of switch 66 is coupled to a first input of a multiplier 70. When switch 66 is set to position 2, the input of switch 66 is not used. When switch 66 is set to position 3, the input of switch 66 is coupled to a memory 72 which stores log-compression look-up tables.

Similarly, the output C' of memory 60 is coupled to the input of a three-position switch 68. When switch 68 is set to position 1, the input of switch 68 is coupled to a second input of multiplier 70. When switch 68 is set to position 2, the input of switch 68 is coupled to scan converter 19. When switch 68 is set to position 3, the input of switch 68 is not used.

In a first operating mode, only the coherence data is displayed. This is accomplished by setting both of switches 66 and 68 to position 2 so that the output signal C' is supplied directly to scan converter 19 and the scan-converted coherence data is displayed on a linear scale by display system 20, shown in FIG. 1.

In a second operating mode, only the amplitude data is displayed. This is accomplished by setting both of switches 66 and 68 to position 3 so that the output signal |A| is supplied directly to log-compression memory 72. The amplitude data is log-compressed in memory 72 and then scan-converted by scan converter 19 in a conventional manner. The log-compressed, scan-converted amplitude data is then displayed by the display system.

In a third operating mode, the product of the coherence and amplitude data is displayed. This is accomplished by setting both of switches 66 and 68 to position 1 so that the output signals |A| and C' are sent to respective inputs of multiplier 70. Multiplier 70 multiplies, sample by sample, the amplitude data by the respective coherence factors. The modified amplitude data is then log-compressed, scan-converted and displayed in conventional manner.

While only certain preferred features of the invention have been illustrated and described, many modifications and changes will occur to those skilled in the art. It is, therefore, to be understood that the appended claims are intended to cover all such modifications and changes as fall within the true spirit of the invention.

I claim:

1. A system for imaging ultrasound scatterers, comprising:

an ultrasound transducer array for transmitting ultrasound beams and detecting ultrasound echoes reflected by said ultrasound scatterers, said transducer array comprising a multiplicity of transducer elements;

transmitter means coupled to said transducer array for forming a transmit beam for each one of a multiplicity of sample volumes;

receiver means comprising a multiplicity of receive channels for receiving respective amplitude signals from said multiplicity of transducer elements;

means for forming an incoherent sum of the received amplitude signals derived from ultrasound echoes reflected by a single sample volume, a respective incoherent sum being formed for each of said multiplicity of sample volumes;

means for displaying an image comprised of pixels wherein the intensity of each pixel is a function of the incoherent sum formed for the corresponding one of said multiplicity of sample volumes;

means for forming a coherent sum of the received amplitude signals derived from ultrasound echoes reflected by a single sample volume, a respective coherent sum being formed for each of said multiplicity of sample volumes; and means for forming a ratio for each of said multiplicity of sample volumes, wherein said ratio equals the absolute value of the coherent sum for a respective sample volume divided by the incoherent sum for said respective sample volume.

2. The system of claim 1, wherein the intensity of each pixel in said displayed image is linearly proportional to the ratio derived for the corresponding one of said multiplicity of sample volumes.

3. The system of claim 1, further comprising means for forming, for each pixel of said image, a product equal to the absolute value of the coherent sum for a respective sample volume multiplied by the ratio for said respective sample volume.

4. The system of claim 3, wherein intensity of each pixel in said displayed image is logarithmically proportional to the product derived for the corresponding one of said multiplicity of sample volumes.

5. The system of claim 1, further comprising a two-dimensional filter for filtering the ratios for said multiplicity of sample volumes prior to display.

6. The system of claim 1, further comprising mapping means for mapping the ratios for said multiplicity of sample volumes prior to display.

7. A method for imaging ultrasound scatterers, comprising the steps of:
   transmitting ultrasound beams focused at respective sample volumes of a multiplicity of sample volumes, at least a plurality of said sample volumes containing ultrasound scatterers;
   detecting, at a multiplicity of detection locations for each sample volume, ultrasound echoes reflected from said multiplicity of sample volumes;
   producing a respective amplitude signal in response to detection of an ultrasound echo from each of said multiplicity of detection locations;
   forming an incoherent sum of the amplitude signals derived from ultrasound echoes reflected by a single sample volume, a respective incoherent sum being formed for each of said multiplicity of sample volumes;
   displaying an image comprised of pixels wherein the intensity of each pixel is a function of the incoherent sum formed for the corresponding one of said multiplicity of sample volumes;
   forming a coherent sum of the amplitude signals derived from ultrasound echoes reflected by a single sample volume, a respective coherent sum being formed for each of said multiplicity of sample volumes; and
   forming a ratio for each of said multiplicity of sample volumes, wherein said ratio equals the absolute value of the coherent sum for a respective sample volume divided by the incoherent sum for said respective sample volume.

8. The method of claim 7, wherein the intensity of each pixel in said displayed image is linearly proportional to the ratio derived for the corresponding one of said multiplicity of sample volumes.

9. The method of claim 7, further comprising the step of forming, for each pixel of said image, a product equal to the absolute value of the coherent sum for a respective sample volume multiplied by the ratio for said respective sample volume.

10. The method of claim 9, wherein the intensity of each pixel in said displayed image is logarithmically proportional to the product derived for the corresponding one of said multiplicity of sample volumes.

11. The method of claim 7, further comprising the step of spatially filtering the ratios for said multiplicity of sample volumes prior to display.

12. The method of claim 7, further comprising the step of mapping the ratios for said multiplicity of sample volumes prior to display.

13. A system for imaging ultrasound scatterers, comprising:
   an ultrasound transducer array for transmitting ultrasound beams and detecting ultrasound echoes reflected by said ultrasound scatterers, said transducer array comprising a multiplicity of transducer elements;
   transmitter means coupled to said transducer array for forming a transmit beam for each one of a multiplicity of sample volumes;
   receiver means comprising a multiplicity of receive channels for receiving respective amplitude signals from said multiplicity of transducer elements;
   means for forming an incoherent sum of the received amplitude signals derived from ultrasound echoes reflected by a single sample volume, a respective incoherent sum being formed for each of said multiplicity of sample volumes;
   means for forming a coherent sum of the received amplitude signals derived from ultrasound echoes reflected by a single sample volume, a respective coherent sum being formed for each of said multiplicity of sample volumes;
   means for forming, for each of said multiplicity of sample volumes, a ratio equal to the absolute value of the coherent sum for a respective sample volume divided by the incoherent sum for said respective sample volume;
   first memory means for storing the absolute value of the coherent sum for each of said multiplicity of sample volumes;
   second memory means for storing the ratio for each of said multiplicity of sample volumes;
   means for forming a product for each of said multiplicity of sample volumes, said product being equal to the absolute value of the coherent sum for a respective sample volume multiplied by the ratio for said respective sample volume;
   means for log-compressing data coupled to the output of the product forming means;
   switching means for coupling said first and second memory means to said product forming means in a first switching state and coupling said first memory means to said log-compressing means in a second switching state; and
   means for displaying an image comprised of pixels, coupled to said log-compressing means.

14. The system of claim 13, wherein the displaying means comprises means for scan-converting data coupled to the output of said log-compressing means, and wherein said switching means is adapted to couple said second memory means to said scan-converting means in a third switching state.

15. The system of claim 13, further comprising a two-dimensional filter for filtering the ratios for said multiplicity of sample volumes prior to display.

16. The system of claim 13, further comprising mapping means for mapping the ratios for said multiplicity of sample volumes prior to display.

* * * * *